(12) United States Patent
Muto et al.

(10) Patent No.: US 9,927,380 B2
(45) Date of Patent: Mar. 27, 2018

(54) DETECTION DEVICE

(71) Applicant: MINEBEA CO., LTD., Kitasaku-gun, Nagano (JP)

(72) Inventors: Akira Muto, Fujisawa (JP); Yasutoshi Obata, Yokohama (JP); Hiroyuki Ohmae, Kawasaki (JP); Kiyoshi Omori, Machida (JP); Yohei Ishii, Chiba (JP)

(73) Assignee: Minebea Co., Ltd., Nagano (JP)

( * ) Notice: Subject to any disclaimer, the term of this patent is extended or adjusted under 35 U.S.C. 154(b) by 91 days.

(21) Appl. No.: 14/670,916

(22) Filed: Mar. 27, 2015

(65) Prior Publication Data
US 2015/0276804 A1    Oct. 1, 2015

(30) Foreign Application Priority Data

Mar. 31, 2014  (JP) ................ 2014-073303

(51) Int. Cl.
*G01N 27/02* (2006.01)
*G01N 27/60* (2006.01)
G01N 27/20 (2006.01)
G01N 27/04 (2006.01)
G01N 27/06 (2006.01)

(52) U.S. Cl.
CPC ............. *G01N 27/02* (2013.01); *G01N 27/60* (2013.01); *G01N 27/04* (2013.01); *G01N 27/041* (2013.01); *G01N 27/06* (2013.01); *G01N 27/20* (2013.01)

(58) Field of Classification Search
CPC ........ G01N 27/02; G01N 27/60; G01N 27/06; G01N 27/20; G01N 27/04; G01N 27/041

USPC .......................................... 324/693
See application file for complete search history.

(56) References Cited

U.S. PATENT DOCUMENTS 3,990,444 A * 11/1976 Vial ..................... A61M 5/142
                                                    128/DIG. 12
4,687,580 A *  8/1987 Malbrancq ............. A61M 1/28
                                                        210/195.2
4,784,643 A * 11/1988 Siretchi ................. A61M 5/365
                                                          604/122

(Continued)

FOREIGN PATENT DOCUMENTS

JP      6110754 S    1/1986
JP      6276440 S    4/1987

(Continued)

OTHER PUBLICATIONS

Wu, Amy, et al. "Modular integration of electronics and microfluidic systems using flexible printed circuit boards." Lab on a Chip 10.4 (2010): 519-521.*

(Continued)

*Primary Examiner* — Jermele M Hollington
*Assistant Examiner* — Christopher McAndrew
(74) *Attorney, Agent, or Firm* — Carrier Blackman & Associates, P.C.; Joseph P. Carrier; Jeffrey T. Gedeon

(57) ABSTRACT

There is provided a detection device including: a detection electrode that is arranged at a position on an arrangement plane near a tubular body; a drive electrode that is arranged on the arrangement plane; and a controller configured to generate lines of electric force between the detection electrode and the drive electrode and to detect a state of the tubular body by detecting lines of electric force entering the detection electrode.

21 Claims, 10 Drawing Sheets

(56) References Cited

U.S. PATENT DOCUMENTS

| | | | | |
|---|---|---|---|---|
| 5,109,202 A * | 4/1992 | Akiba | G01N 27/12 | 174/11 R |
| 5,602,486 A * | 2/1997 | Novak | G01B 7/087 | 324/519 |
| 6,491,805 B1 * | 12/2002 | Gordon | G01N 27/4473 | 204/409 |
| 6,593,143 B1 * | 7/2003 | Gordon | B04B 5/02 | 422/64 |
| 7,483,140 B1 * | 1/2009 | Cho | G01N 21/553 | 356/445 |
| 7,497,997 B2 * | 3/2009 | Glezer | B01L 3/5027 | 422/504 |
| 7,850,835 B2 * | 12/2010 | Amshey | G01N 27/44795 | 204/518 |
| 8,400,172 B2 * | 3/2013 | Wilson | G01N 17/04 | 324/691 |
| 8,999,724 B2 * | 4/2015 | Holt | G01N 27/227 | 422/68.1 |
| 2004/0203239 A1 * | 10/2004 | Gilton | B01D 61/18 | 438/689 |
| 2006/0073489 A1 * | 4/2006 | Li | B01D 57/02 | 435/6.11 |
| 2007/0291473 A1 * | 12/2007 | Traynor | A01K 11/00 | 362/106 |
| 2010/0030387 A1 * | 2/2010 | Sen | A61M 5/14232 | 700/282 |
| 2010/0261287 A1 * | 10/2010 | Holt | G01N 27/3276 | 436/149 |
| 2011/0100804 A1 * | 5/2011 | Krone | B08B 17/00 | 204/242 |
| 2011/0102002 A1 * | 5/2011 | Riehl | B82Y 30/00 | 324/693 |
| 2011/0297545 A1 * | 12/2011 | Latham | G01N 27/44739 | 204/464 |
| 2012/0182027 A1 * | 7/2012 | Jagiella | G01N 27/06 | 324/654 |
| 2014/0055149 A1 * | 2/2014 | Zhu | G01R 27/2623 | 324/693 |
| 2014/0352431 A1 * | 12/2014 | Leclerc | G01C 19/5712 | 73/504.04 |

FOREIGN PATENT DOCUMENTS

| | | |
|---|---|---|
| JP | H04-110648 A | 4/1992 |
| JP | 2007-296134 A | 11/2007 |
| JP | 2012-205866 A | 10/2012 |
| JP | 2014029315 A | 2/2014 |

OTHER PUBLICATIONS

Office Action dated Jan. 20, 2016 in the corresponding Japanese patent application No. 2014-73303.
Office Action dated Jun. 24, 2015 in the corresponding Japanese Patent Application No. 2014-73303.

* cited by examiner

DETECTION DEVICE

BACKGROUND OF THE INVENTION

1. Field of the Invention

The present invention relates to a detection device which detects a state of a tubular body. Examples of such state are: presence or absence of a tubular body at a specified position type of diameter (inside diameter, outside diameter, and wall thickness) of the tubular body; presence or absence of a fluid such as liquid flowing through the tubular body; the type of the fluid, in particular liquids; presence or absence of an air bubble in a liquid; and state related to the tubular body at the specified position and to a fluid, in particular liquid, flowing through the tubular body.

2. Description of the Related Art

Conventionally, the devices disclosed in JP-A-2012-205866 and JP-A-2007-296134 have been developed as a detection device of this kind, particularly, a detection device for detecting an air bubble in liquid such as a medical solution or dialysis solution flowing through a transfusion tube (tubular body).

The detection device disclosed in JP-A-2012-205866 is a device in which an ultrasonic sensor is used as means for detecting an air bubble in a transfusion tube, and the presence/absence of such an air bubble is determined based on the propagation efficiency of ultrasonic waves in the transfusion.

In the detection device disclosed in JP-A-2007-296134, a capacitance is configured in which members that cause opposed portions of the outer circumferential surface of a transfusion tube to be flattened, and that nip the tube are used as one set of electrodes, and thick portions of the transfusion tube, and the volume part of the transfusion tube sandwiched between the one set of electrodes are used as a capacitor capacitance. The device detects an air bubble entering the transfusion tube based on the capacitor capacitance which varies in accordance with the presence/absence state of liquid in the volume part.

However, in the detection device which is disclosed in JP-A-2012-205866, and in which an ultrasonic sensor is used, ultrasonic transmission and reception parts must be placed so as to be opposed to each other. Therefore, the sensor is difficult to be produced, and its production cost is high. The device has a complicated structure, and hence it is difficult to clean the device. In order to ensure the accuracy, moreover, the transfusion tube must be in close contact with a sensor portion. Consequently, there is a possibility that the durability of the transfusion tube is lowered.

In the detection device which is disclosed in JP-A-2007-296134, and which operates based on the capacitor capacitance, the transfusion tube must be deformed, and hence there is a possibility that the transfusion tube is damaged or its lifetime is shortened. Moreover, the electrodes must be oppositely placed. Therefore, the device has a complicated structure, and hence it is difficult to clean the device.

SUMMARY OF THE INVENTION

The present invention has been made in view of the above circumstances, and one of the objects of the invention to provide a detection device in which electrodes are not necessary to be oppositely placed, which can be produced easily and economically, has a simple structure, and is easy to be cleaned, and in which a tubular body that is a target of the state detection is requested only to be placed on an electrode surface, and therefore the tubular body can be prevented from being damaged, and also from being shortened in lifetime. More particularly, it is an object of the invention to provide a detection device which is suitable for detecting an air bubble in liquid flowing through a transfusion tube (tubular body).

According to an illustrative embodiment of the present invention, there is provided a detection device including: a detection electrode that is arranged at a position on an arrangement plane near a tubular body; a drive electrode that is arranged on the arrangement plane; and a controller configured to generate lines of electric force between the detection electrode and the drive electrode and to detect a state of the tubular body by detecting lines of electric force entering the detection electrode.

DETAILED DESCRIPTION

Figure 1:
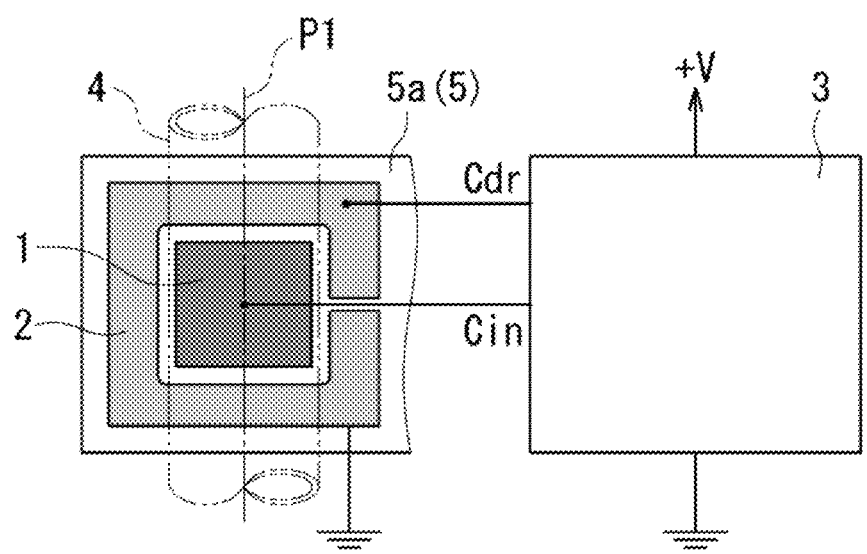
FIG. 1 is a block diagram of detection device according to a first embodiment of the present invention.

Hereinafter, embodiments of the invention will be described with reference to the drawings. In the figures, the same reference numerals denote identical or equivalent components.

Figure 2:
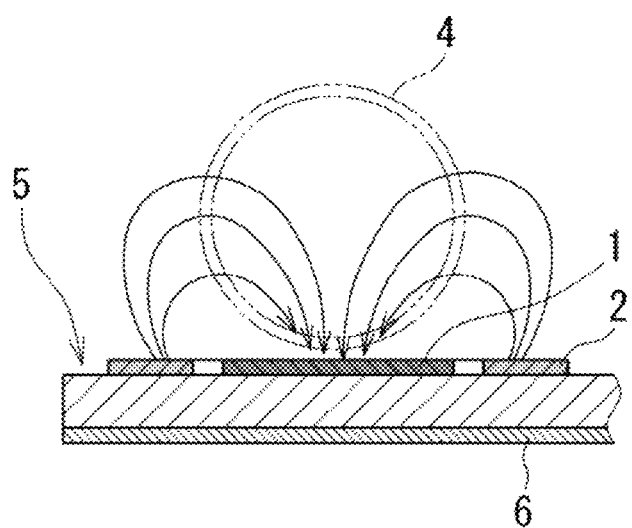
FIG. 2 is a cross-sectional diagram of the detection device according to the first embodiment.

FIG. 1 is a block diagram of a detection device according to a first embodiment of the present invention. FIG. 2 is a cross-sectional diagram of the detection device, and FIG. 3 is a schematic perspective view of the detection device.

Figure 3:
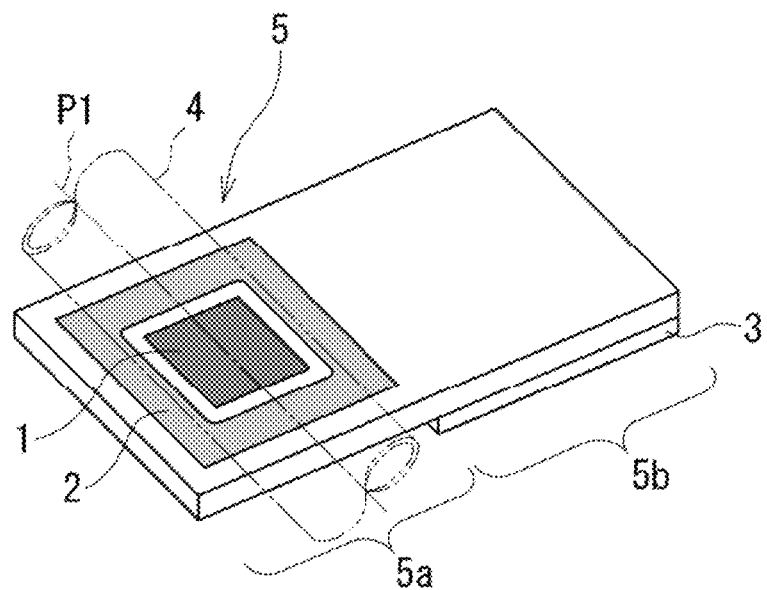
FIG. 3 is a schematic perspective view of the detection device according to the first embodiment.

As shown in FIGS. 1 to 3, the detection device is provided with a detection electrode 1, a drive electrode 2, and a controller 3, and detects the state of a tubular body 4 which is positioned at a predefined specified position P1, and that is in the vicinity of the detection electrode 1. The specified position P1 is set to be in a three-dimensional space as described later. In FIGS. 1 and 3, the center position of the specified position P1 is shown by a single-dot chain line labeled P1, and an outline of the tubular body 4 is shown by a double-dot chain line.

The detection electrode 1 is placed in a sensor region 5a on a surface of a sensor board 5 which is made of an insulator. The drive electrode 2 is placed on the same plane (on the same plane or on the same curved plane, in the embodiment, on the same plane) as the plane where the detection electrode 1 is placed, or namely placed on the surface of the sensor board 5. Specifically, the drive electrode is placed in the sensor region 5a, and at an adjacent position which is separated by an adequate distance from the detection electrode 1.

The controller 3 is a circuit section in which a detection electrode terminal Cin is connected to the detection electrode 1, a drive electrode terminal Cdr is connected to the drive electrode 2, which generates lines of electric force (electric field) between the drive electrode 2 and the detection electrode 1, and which detects lines of electric force entering the detection electrode 1. The controller 3 is placed in a circuit component area 5b which is set on a bottom face of the sensor board 5, and which corresponds to an area adjacent to the sensor region 5a in the surface of the sensor board 5.

A ground electrode 6 is placed on the bottom face of the sensor board 5. The ground electrode 6 is placed in order to prevent the lines of electric force from leaking toward the bottom face of the sensor board 5, thereby preventing the controller 3 from reacting (erroneously operating) with a motion or the like of a structure (not shown) on the side of the bottom face of the sensor board 5 which is not a target of the state detection.

The specified position P1 is set at a position in a space where the lines of electric force can be interrupted, and where is in the vicinity of the detection electrode 1. The specified position P1 is a position where the tubular body 4 which is a target of the state detection abuts the detection electrode 1, or that where the tubular body does not abut the detection electrode. Usually, the specified position is set at a position at which the tubular body 4 abuts or is in close proximity to the detection electrode 1. Therefore, the tubular body 4 is not set at a position where the tubular body is pressed against by a degree which causes deformation or in close contact with the detection electrode 1. In other words, the tubular body 4 is requested to be positioned on the electrode surface of the detection electrode 1.

In the case where, as shown in FIG. 2, the tubular body 4 is positioned in a place where the tubular body does not abut but is in close proximity to the detection electrode 1 (separated from the detection electrode 1), a positioning table (not shown) may be used.

The arcuate arrows in FIG. 2 indicate lines of electric force. The arc lines shown in FIG. 2 represent the lines of electric force generated by the chive electrode 2 to the detection electrode 1. When the number of lines of electric force entering the detection electrode 1 is increased or decreased, the electrostatic capacitance between the electrodes 1, 2 is changed, and the state of the tubular body 4 which is positioned at a position on the electrode surface of the detection electrode 1 (a position at which the tubular body abuts or is in close proximity to the detection electrode 1) is detected by the controller 3.

Here, the above term "state of the tubular body 4" means any one of: presence or absence of the tubular body 4 at the specified position P1; type of diameter (inside diameter, outside diameter, and wall thickness) of the tubular body 4; presence or absence of a fluid such as liquid flowing through the tubular body 4; the type of the fluid, in particular liquid; presence or absence of an air bubble in a liquid; and state related to the tubular body at the specified position and to a fluid, in particular liquid, flowing through the tubular body. The type of the diameter of the tubular body means, for example, one of the types of tubular bodies which are classified according to the diameter size. For example, the type of the liquid means a medical solution, a dialysis solution, water, oil, or the like.

As the first embodiment, an example will be described in which the detection device is used for detecting an air bubble in liquid such as a medical solution, a dialysis solution, or the like flowing through a transfusion tube employed in a medical transfusion pump apparatus. The tubular body 4 indicates a transfusion tube.

The detection of an air bubble is the detection of the presence or absence of an air bubble. In the first embodiment, the size of an air bubble and the number of air bubbles (or changing amounts of such values) in liquid flowing through the transfusion tube 4 can be detected. When, for example, thresholds are set with respect to the detection values, therefore, the presence/absence of an air bubble can be detected based on an adequate detection value.

Figure 4A:
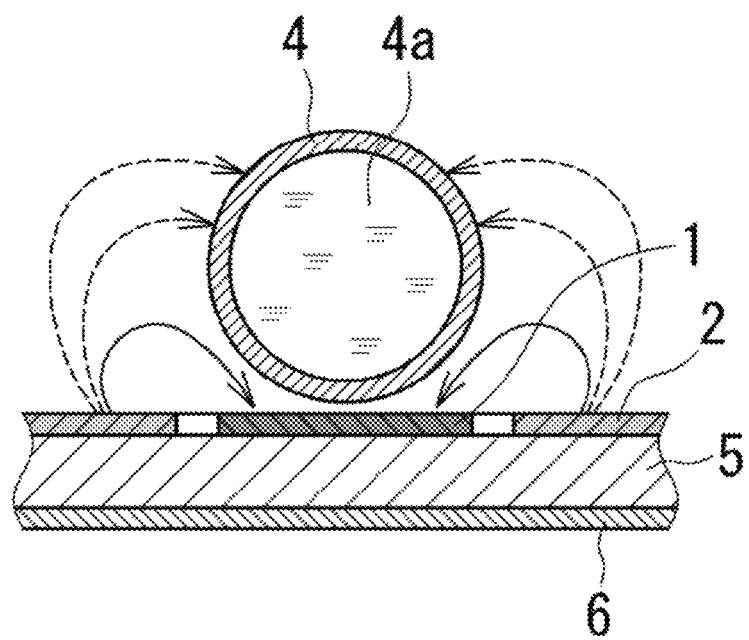
FIGS. 4A and 4B are operational diagrams of the detection device according to the first embodiment.
Figure 4B:
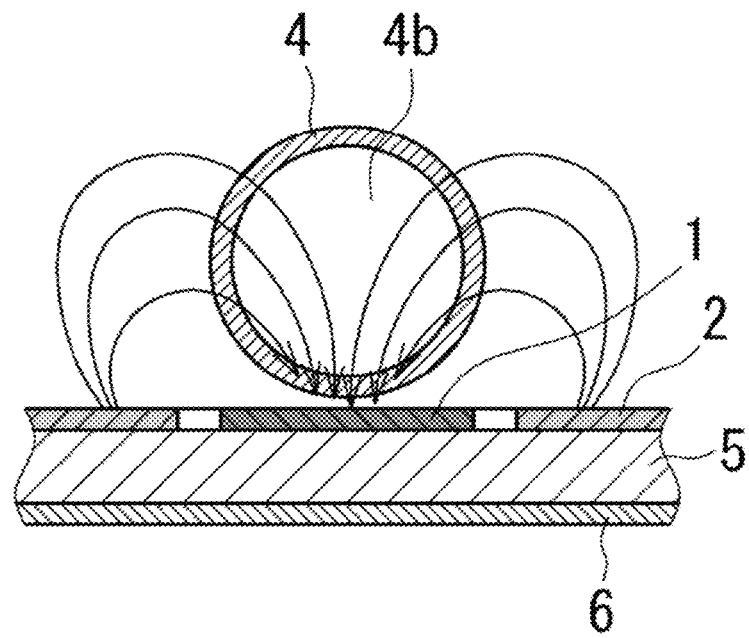

Next, the operation of the detection device of the first embodiment will be described. FIGS. 4A and 4B are operational diagrams of the detection device of the first embodiment. FIG. 4A shows a state where no air bubble exists in liquid 4a flowing through the transfusion tube 4. In another words, FIG. 4A shows a state where the transfusion tube 4 is filled with the liquid 4a. FIG. 4B shows a state where an air bubble 4b exists in the liquid 4a flowing through the transfusion tube 4. FIG. 4B shows a state where the air bubble 4b exists so as to occupy the whole cross-section of the transfusion tube 4.

When the operation of the controller 3 shown in FIGS. 1 and 3 is started, many lines of electric force are generated between the drive electrode 2 and the detection electrode 1 as shown in FIG. 2.

Here, it is assumed that, as shown in FIGS. 4A and 4B, the transfusion tube 4 is positioned at the specified position P1 (see FIGS. 1 and 3), in the first embodiment, at a position which is substantially in the middle of the upper surface of the detection electrode 1, and which is in close proximity to the detection electrode 1. When the transfusion pump apparatus is operated under this condition, transfusion is started. When transfusion is smoothly performed, the liquid 4a flows in a state where it fills the transfusion tube 4. As shown in FIG. 4A, namely, the air bubble 4b does not exist in the liquid 4a, and the lines of electric force (in the figures, indicted by the arcuate arrows, the same shall apply hereinafter) which are directed from the drive electrode 2 toward the detection electrode 1 are interrupted mainly by the liquid 4a filling the transfusion tube 4. Therefore, the number of the lines of electric force is reduced.

When, as shown in FIG. 4B, the air bubble 4b exists in the liquid 4a flowing through the transfusion tube 4 [in FIG. 4B, the air bubble 4b exists so as to occupy the whole cross-section of the transfusion tube 4], the number of the lines of electric force is less reduced by the air bubble 4b.

In the case where the air bubble 4b does not exist in the liquid 4a, namely, the number of the lines of electric force is small, and, in the case where the air bubble 4b exists, the number is large. The electrostatic capacitance between the electrodes 1, 2 is changed in accordance with the increased/decrease of the number of the lines of electric force. When the electrostatic capacitance in the case where the air bubble 4b does not exist in the liquid 4a is measured, therefore, a detection result indicating that the air bubble 4b does not exist is obtained by the controller 3 shown in FIGS. 1 and 3. When the electrostatic capacitance in the case where the air bubble 4b exists is measured, a detection result indicating that the air bubble 4b exists is obtained. Alternatively an adequate threshold may be set between the electrostatic capacitance in the case where the air bubble 4b does not exist in the liquid 4a, and that in the case where the air bubble 4b exists, and the presence/absence of the liquid 4a may be detected depending on whether the measured value exceeds the threshold or not.

Alternatively the electrostatic capacitance in the case where the air bubble 4b does not exist in the liquid 4a may be set as the normal state, and that in the case where the air bubble 4b exists in the liquid 4a may be set as the abnormal state. The detection result indicating whether the air bubble 4b exists or not may be output as one of the normal state and the abnormal state.

In the above-described first embodiment, the detection electrode 1 and the drive electrode 2 are placed on the same plane (the surface of the sensor board 5), or namely the electrodes 1, 2 are not necessary to be opposedly placed. Therefore, the detection device can be produced easily and economically, and the structure is not complicated but simplified so that cleaning is easily performed. Since the detection device is easy to be cleaned, the device is particularly effective in application to a detection device for a medical apparatus in which a high level of cleanliness is required.

When the transfusion tube (tubular body) 4 is to be positioned, it is necessary simply to position the transfusion tube on the electrode surface of the detection electrode 1. Namely, it is not required to bring the transfusion tube 4 into close contact with the detection electrode 1, or to deform the transfusion tube 4. Therefore, damage to transfusion tube 4 and a shortened lifetime can be prevented. Particularly, the detection device is effective in detecting the air bubble 4b entering the transfusion tube 4 (liquid 4a).

In the above-described first embodiment, the placement positions and shapes (electrode patterns) of the detection electrode 1 and the drive electrode 2 are formed as shown in FIGS. 1 and 3. Namely, one detection electrode 1 is placed substantially in the middle of the sensor region 5a on the surface of the sensor board 5 while being formed into an approximately square shape, and forming an appropriate gap between the electrodes, one drive electrode 2 is placed so as to surround the detection electrode 1 in the sensor region 5a.

Figure 5A:
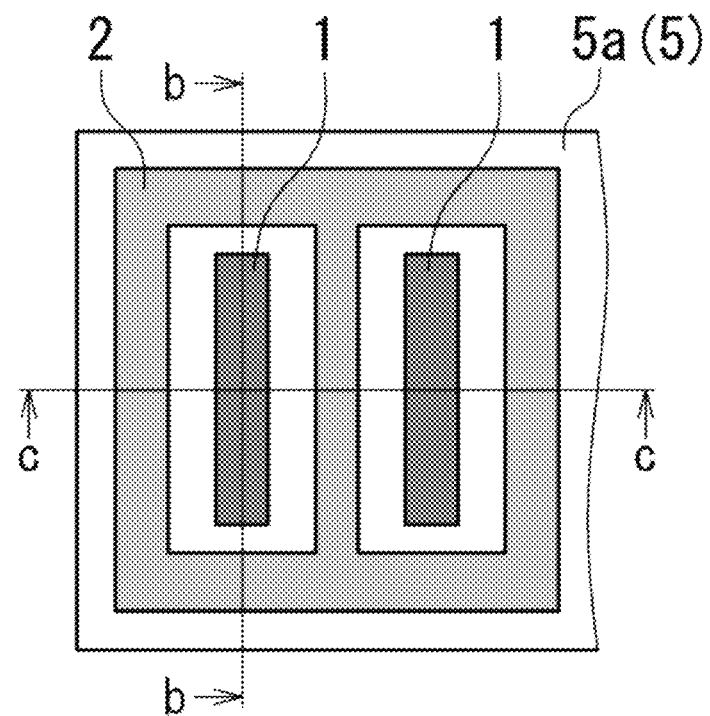
FIG. 5A is a plan view illustrating a configuration of main portions of a detection device according to a second embodiment of the present invention.
Figure 6A:
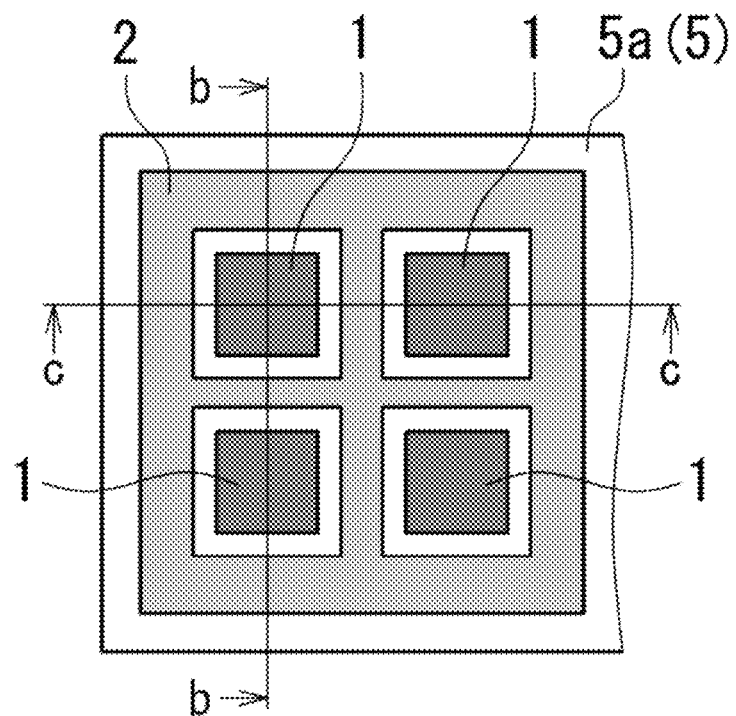
FIG. 6A is a plan view illustrating a configuration of main portions of a detection device according to a third embodiment of the present invention.
Figure 7A:
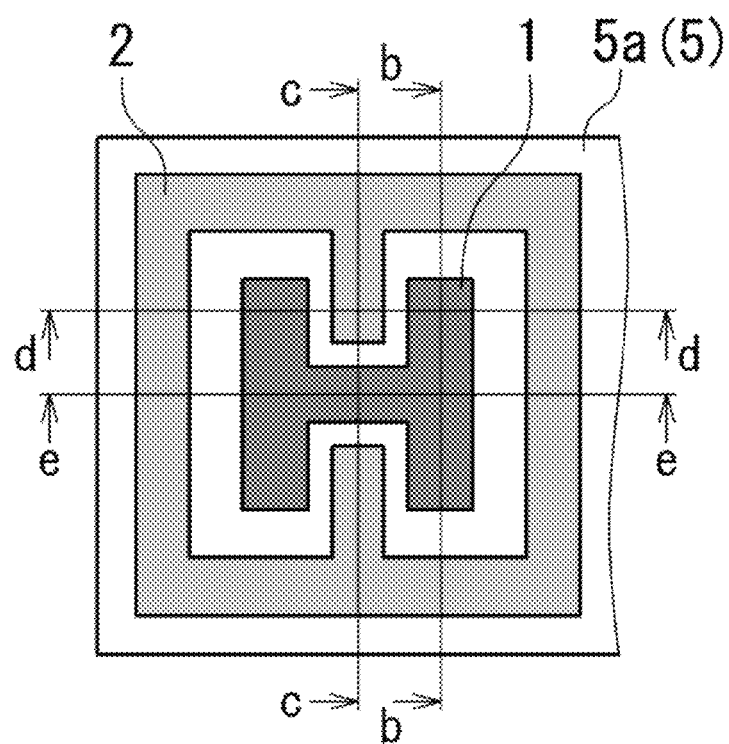
FIG. 7A is a plan view illustrating a configuration of main portions of a detection device according to a fourth embodiment of the present invention.

However, the electrode patterns of the detection device of the invention are not limited to those shown in FIGS. 1 and 3. As second, third, and forth embodiments, the electrode patterns may be formed as shown in FIGS. 5A, 6A, and 7A. As fifth and sixth embodiments, moreover, the electrode patterns may be formed as shown in FIGS. 8 and 9.

As shown in FIG. 5A, the electrode patterns may be formed so that a pair of strip-like detection electrodes 1, 1 are placed so as to be laterally juxtaposed formed with a predetermined gap, and one drive electrode 2 is placed so as to surround the whole detection electrodes 1, 1, and to separate the detection electrodes 1, 1 from each other.

As shown in FIG. 6A, the electrode patterns may be formed so that four detection electrodes 1 having an approximately square shape are placed so as to be vertically and laterally symmetrical formed with a predetermined gap, and one drive electrode 2 is formed between the gap and to surround the four detection electrodes 1 as shown in FIG. 6A.

Figure 8:
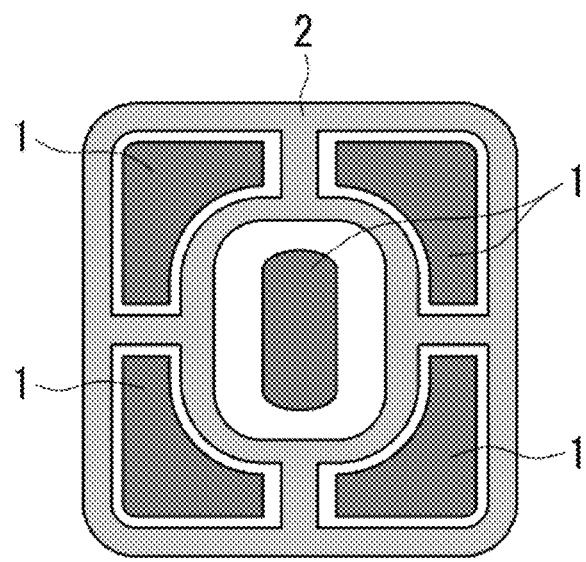
FIG. 8 is a plan view illustrating a configuration of main portions of a detection device according to a fifth embodiment of the present invention.
Figure 9:
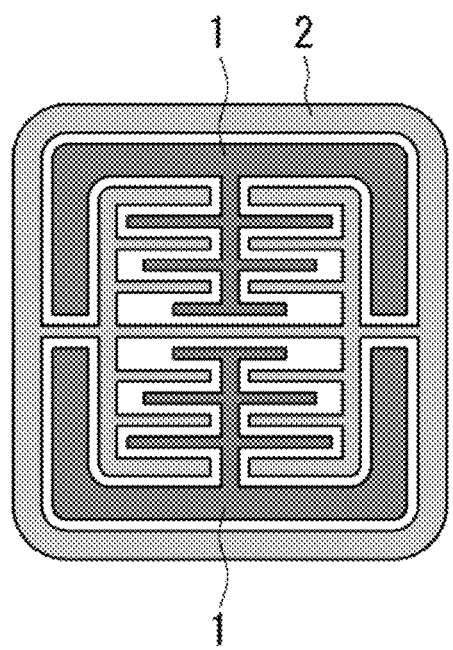
FIG. 9 is a plan view illustrating a configuration of main portions of a detection device according to a sixth embodiment of the present invention.

As shown in FIG. 7A, the electrode patterns may be formed so that one detection electrode 1 having a shape which is similar to a letter "H" is placed, and one drive electrode 2 is placed so that it surrounds the whole detection electrode 1 formed with an adequate gap, and partition portions extend into detection electrode nonexisting portions [portions on line c-c in FIG. 7A] which are separated by the lateral line of the character "H" of the detection electrode 1 and formed above and below the lateral line, As shown in FIG. 5, the electrode patterns may be formed so that, in the electrode pattern in which the drive electrode 2 is formed in a form similar to the shape in FIG. 5, one further detection electrode 1 is placed in the middle portion of the shape in FIG. 8 formed with an adequate gap with respect to the drive electrode 2.

As shown in FIG. 9, the electrode patterns may be formed so that a pair of detection electrodes 1 in each of which many branch portions are formed inside the outer circumferential portion of a substantially "U"-like shape are placed while the open sides of the "U"-like shapes are opposed to each other, and one drive electrodes 2 is placed so as to surround the whole paired detection electrodes 1 formed with an adequate gap, to inwardly extend from gaps of opposed portions of the pair of detection electrodes 1, and to cause the branch portions to be alternately positioned between the many branch portions of the pair of detection electrodes 1.

All of the detection electrodes 1 and drive electrodes 2 shown in FIGS. 5A, 6A, and 7A are placed in the sensor region 5a in the surface of the sensor board 5. Similarly, also the detection electrodes 1 and drive electrodes 2 shown in FIGS. 8 and 9 are placed in the sensor region 5a in the surface of the sensor board 5. In FIGS. 8 and 9, however, the sensor region 5a is not illustrated.

In each of the second, third, fifth, and sixth embodiments [embodiments shown in FIGS. 5A, 6A, 8, and 9], the plurality of detection electrode 1 are disposed, and connected to the detection electrode terminal C in (see FIG. 1) of the controller 3.

Figure 5B:
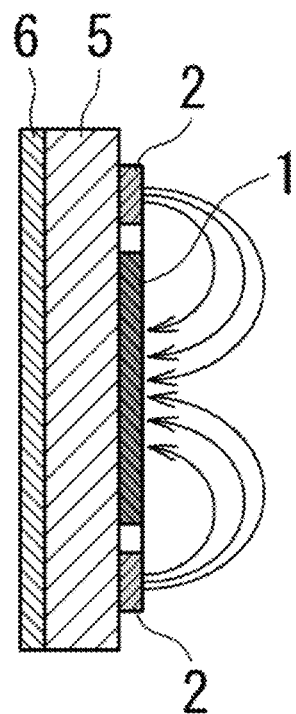
FIGS. 5B and 5C are cross-sectional diagrams of the detection device according to the second embodiment.
Figure 5C:
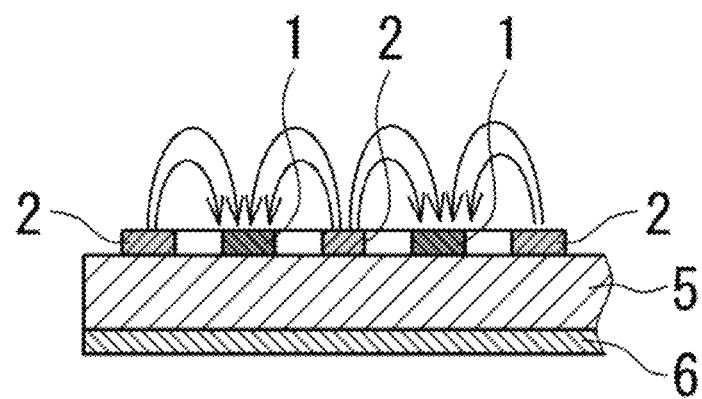

FIG. 5B is a view showing lines of electric force in a section taken along line b-b in FIG. 5A, and FIG. 5C is a view showing lines of electric force in a section taken along line c-c in FIG. 5A.

Figure 6B:
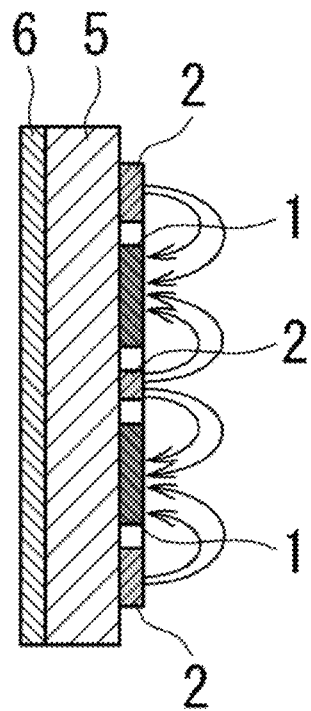
FIGS. 6B and 6C are cross-sectional diagrams of the detection device according to the second embodiment.
Figure 6C:
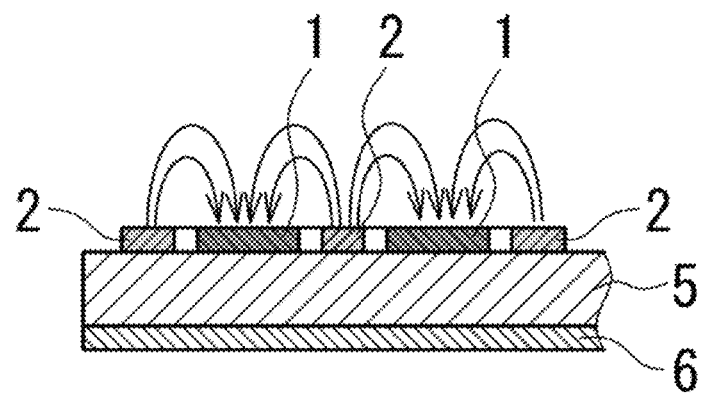

FIG. 6B is a view showing lines of electric force in a section taken along line b-b in FIG. 6A, and FIG. 6C is a view showing lines of electric force in a section taken along line c-c in FIG. 6A.

Figure 7B:
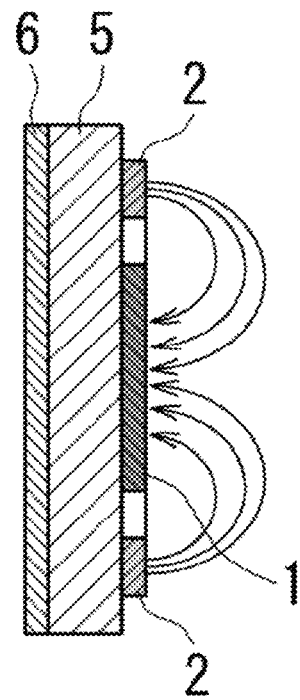
FIGS. 7B to 7E are cross-sectional diagrams of the detection device according to the fourth embodiment.
Figure 7C:
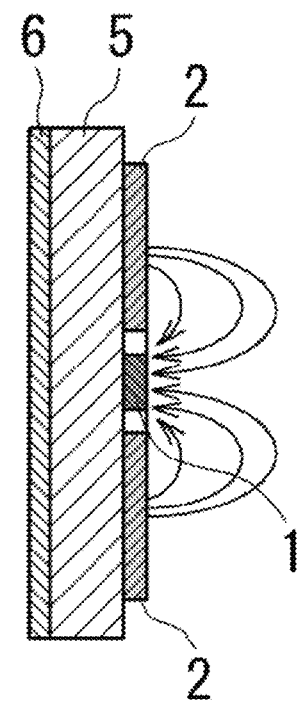
Figure 7D:
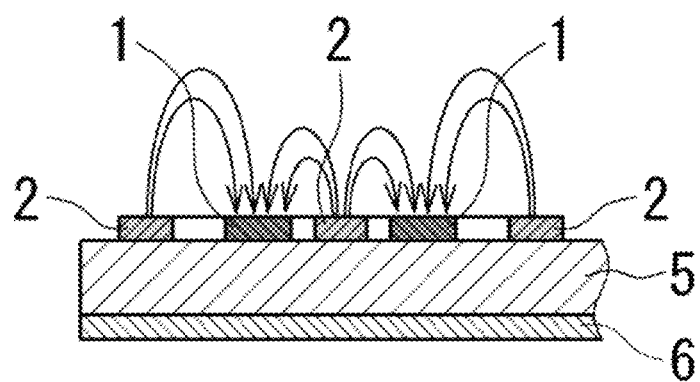
Figure 7E:
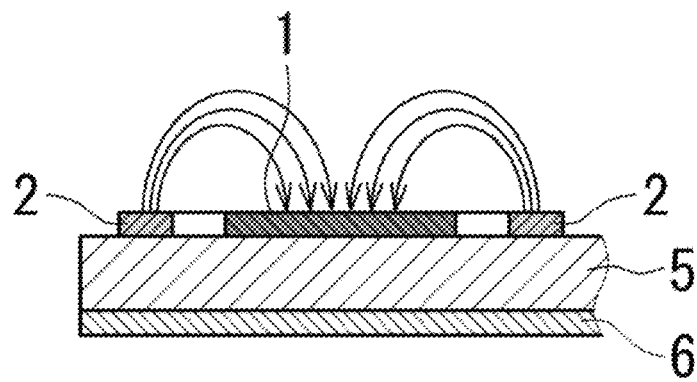

FIG. 7B is a view showing lines of electric force in a section taken along line b-b in FIG. 7A, FIG. 7C is a view showing lines of electric force in a section taken along line c-c in FIG. 7A, FIG. 7D is a view showing lines of electric force in a section taken along line d-d in FIG. 7A, and FIG. 7E is a view showing lines of electric force in a section taken along line e-e in FIG. 7A.

When the electrode patterns of the detection electrode 1 and the drive electrode 2 are formed as shown in FIGS. 5A, 6A, and 7A or FIGS. 8 and 9, various numbers of lines of electric force, or lines of electric force of various directions can be generated from a wide variety of positions. When the electrode patterns are adequately selected in accordance with the diameter, material, and the like of the transfusion tube (tubular body) 4 which is a target of the state detection, or the specified position P1 at which the detection electrode 1 is positioned, therefore, it is possible to realize cost-effective air bubble detection.

Figure 10:
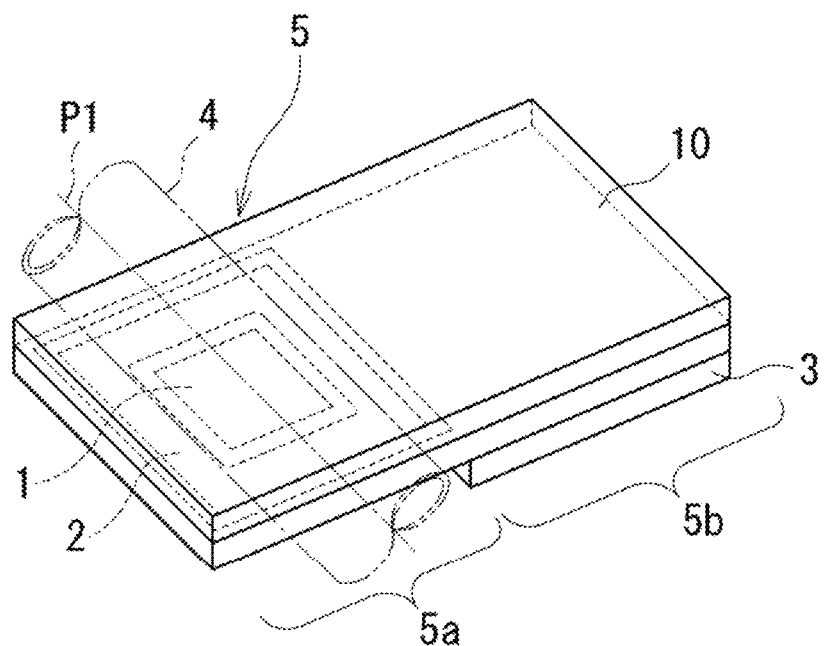
FIG. 10 is a schematic perspective view of a detection device according to a seventh embodiment of the present invention.
Figure 11:
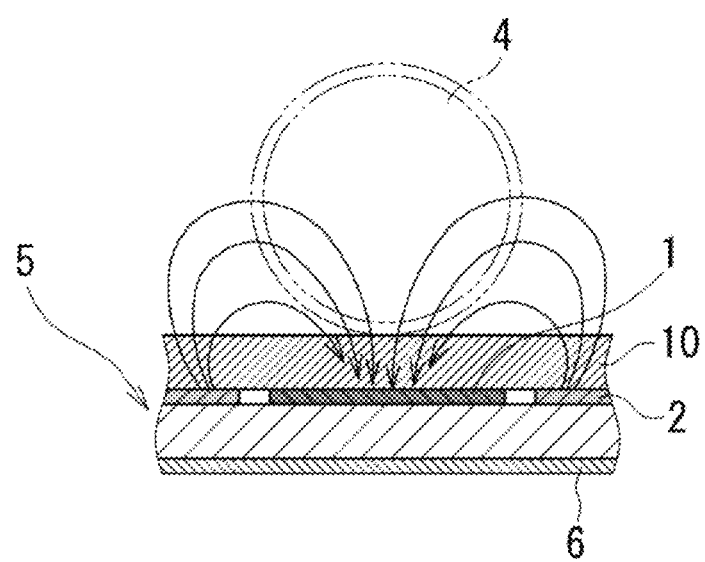
FIG. 11 is a cross-sectional diagram illustrating the configuration of main portions of the detection device according to the seventh embodiment.

FIG. 10 is a schematic perspective view of a seventh embodiment of the detection device of the invention, and FIG. 11 is a cross-sectional diagram of main portions of the embodiment.

In the seventh embodiment, the sensor board 5 is covered by a cover so as to sandwich the detection electrode 1 and the drive electrode 2. In the illustrated example, the whole surface of the sensor board 5 including the sensor region 5a of the sensor board 5 where the detection electrode 1 and the drive electrode 2 are placed is covered by a resin made cover 10.

According to the seventh embodiment, as seen in FIG. 11, the transfusion tube (tubular body) 4 is used in a state where it is placed on the resin made cover 10, and therefore cleaning, is further facilitated. As seen from FIGS. 10 and 11, the detection electrode 1 and the chive electrode 2 are covered by the resin made cover 10. Therefore, a short circuit can be prevented from occurring caused by penetration of liquid such as leaking transfusion into the positions of the electrodes 1, 2 (sensor region 5a), and the safety can be enhanced.

The further facilitation of the cleaning and enhancement of the safety are very useful in application of the seventh embodiment to a detection device for a medical apparatus.

The cover which covers the sensor board 5 is not limited to the resin made cover 10. A material which is insulative, water resistant, and waterproof, and which does not largely reduce the number of lines of electric force entering the detection electrode 1 is selected as the material of the cover.

When the number of generated lines of electric force is increased (the density becomes high), it is possible to enhance the sensitivity of the air bubble detection. Therefore, a board-electrode pattern coupled member is produced in which a flexible printed circuit board (FPC) is used as the sensor board 5, and the electrode patterns of the detection electrode 1 and the drive electrode 2 that are deformable in the same manner as the board are formed on the board. When the detection device is configured by wrapping the transfusion tube 4 with the board-electrode pattern coupled member, it is possible to realize a further enhanced sensitivity.

Although the case where the detection device of the present invention is applied to an air bubble detection apparatus has been described as the first embodiment, the present invention is not limited to this.

In the present invention, basically, the principle of an electrostatic capacitance type sensor is used. Therefore, the invention can detect a material (solid, liquid, or gas) which can change an electrostatic capacitance (number of lines of electric force), and the state of the material, and can be applied to a detection device which performs such detection. Specifically, the present invention can be applied also to a detection device which detects the presence/absence of a tubular body at a specified position which is in the vicinity of the detection electrode, and which is predetermined, the type of the diameter (inside diameter, outside diameter, and wall thickness) of the tubular body (the kinds of tubular bodies which are classified according to the diameter size, and the like), the presence/absence of a fluid such as liquid flowing through the tubular body, or the kind of the fluid, particularly the liquid (a medical solution, a dialysis solution, water, oil, or the like).

What is claimed is:

1. A detection device comprising:
   a base plate having a first surface and a second surface opposite to the first surface, the base plate being defined with a first region and a second region that is adjacent to the first region;
   a detection electrode that is arranged at a position on an arrangement plane defined on the first surface of the base plate within the first region;
   a single drive electrode that is arranged on the arrangement plane at a position entirely surrounding an in-plane circumference of the detection electrode; and
   a controller that is arranged on the base plate within the second region and on the second surface, the controller being configured to:
      drive the drive electrode to generate lines of electric force between the detection electrode and the drive electrode;
      detect lines of electric force passing through a tubular body and entering the detection electrode; and
      detect a state of the tubular body based on the detected lines of electric force entering the detection electrode.

2. The detection device according to claim 1,
   wherein the state of the tubular body includes any one of: presence or absence of the tubular body at the specified position; type of diameter of the tubular body; presence or absence of a fluid flowing through the tubular body; type of the fluid; and presence or absence of a bubble in the fluid.

3. The detection device according to claim 1,
   wherein a surface of the detection electrode is configured to be a flat surface, and
   wherein the tubular body is arranged at a specified position that is defined at a position above the surface of the detection electrode, and at which the tubular body abuts or is in close proximity to the surface of the detection electrode.

4. The detection device according to claim 1 further comprising:
   a cover configured to cover the detection electrode and the drive electrode.

5. The detection device according to claim 4,
   wherein the cover is made of non-conductive material.

6. The detection device according to claim 5,
   wherein the cover is made of resin material.

7. The detection device according to claim 1 further comprising:
   a ground electrode that is arranged on the second surface of the base plate,
   wherein the drive electrode is arranged at a position where the detection electrode is interposed or at a position surrounding the detection electrode, and
   wherein the lines of electric force are generated from a plurality of places and in a plurality of directions.

8. The detection device according to claim 7,
   wherein the base plate is configured by a flexible printed circuit board.

9. The detection device according to claim 8,
   wherein the flexible printed circuit board is configured to be wrapped around the tubular body facing the arrangement plane toward the tubular body.

10. The detection device according to claim 1,
    wherein the tubular body is a transfusion tube, and
    wherein the controller is configured to detect a bubble in liquid flowing through the transfusion tube.

11. A detection device comprising:
a base member having a first surface and a second surface opposite to the first surface, the first surface being faced to a tubular body;
a first electrode provided on the first surface of the base member;
a single second electrode provided on the first surface of the base member and entirely surrounding an in-plane circumference of the first electrode; and
a controller disposed on the second surface configured to generate lines of electric force between the first electrode and the second electrode and to detect a state of the tubular body by detecting lines of electric force entering one of the first and second electrodes.

12. The detection device according to claim 11 further comprising:
a cover member provided above the first and second electrodes and covers the first and second electrodes.

13. The detection device according to claim 11,
wherein the first surface of the base member has a flat surface.

14. The detection device according to claim 11,
wherein the first surface of the base member has a shape corresponding to an outer shape of the tubular body.

15. The detection device according to claim 14,
wherein the first surface of the base member has a curved surface.

16. The detection device according to claim 11 further comprising:
a third electrode provided on the second surface of the base member and grounded to a ground potential.

17. The detection device according to claim 11,
wherein one of the first and second electrodes is substantially surrounded by the other of the first and second electrodes.

18. The detection device according to claim 17,
wherein one of the first and second electrodes has a lattice or a comb-like configuration.

19. A detection device comprising:
a base plate having a first surface and a second surface opposite to the first surface, the base plate being defined with a first region and a second region that is adjacent to the first region;
a detection electrode that is arranged at a position on an arrangement plane defined on the first surface of the base plate within the first region;
a single drive electrode that is arranged on the arrangement plane at a position entirely surrounding an in-plane circumference of the detection electrode, the drive electrode being configured to produce an electric field between the detection electrode and the drive electrode; and
a controller that is arranged on the base plate within the second region and on the second surface, the controller being configured to:
detect a state of tubular body in the electric field based on an electrostatic capacity between the detection electrode and the drive electrode.

20. The detection device according to claim 1,
wherein the controller is arranged on the second surface of the base plate within the second region.

21. The detection device according to claim 19,
wherein the controller is arranged on the second surface of the base plate within the second region.

* * * * *